(12) United States Patent
Coleman

(10) Patent No.: US 7,741,244 B2
(45) Date of Patent: *Jun. 22, 2010

(54) FUNGICIDE COMPOSITIONS

(76) Inventor: Robert D. Coleman, 4249 Mariner La., Okemos, MI (US) 48864

( * ) Notice: Subject to any disclaimer, the term of this patent is extended or adjusted under 35 U.S.C. 154(b) by 1060 days.

This patent is subject to a terminal disclaimer.

(21) Appl. No.: 10/501,026

(22) PCT Filed: Jan. 9, 2003

(86) PCT No.: PCT/US03/00608

§ 371 (c)(1),
(2), (4) Date: Jul. 9, 2004

(87) PCT Pub. No.: WO03/059063

PCT Pub. Date: Jul. 24, 2003

(65) Prior Publication Data

US 2004/0266852 A1    Dec. 30, 2004

Related U.S. Application Data

(60) Provisional application No. 60/347,208, filed on Jan. 9, 2002.

(51) Int. Cl.
| | |
|---|---|
| A01N 25/00 | (2006.01) |
| A01N 37/00 | (2006.01) |
| A01N 65/00 | (2009.01) |
| A01N 33/18 | (2006.01) |
| A01N 25/24 | (2006.01) |
| A01N 25/34 | (2006.01) |
| A61K 31/01 | (2006.01) |
| A61K 31/02 | (2006.01) |
| A61K 47/00 | (2006.01) |
| A61K 31/04 | (2006.01) |
| A01N 29/02 | (2006.01) |

(52) U.S. Cl. ............... 504/116.1; 504/189; 504/320; 514/740; 514/741; 514/761; 514/762; 514/784; 514/789; 424/404; 424/405; 424/407

(58) Field of Classification Search .......... 504/116.1, 504/189, 320
See application file for complete search history.

(56) References Cited

U.S. PATENT DOCUMENTS

| | | | |
|---|---|---|---|
| 3,947,589 A * | 3/1976 | Misato et al. ............ 514/563 |
| 4,430,381 A | 2/1984 | Harvey et al. | |
| 4,436,547 A | 3/1984 | Sampson | |
| 4,581,373 A | 4/1986 | Mulqueen et al. | |
| 4,599,233 A | 7/1986 | Misato et al. | |
| 4,975,110 A * | 12/1990 | Puritch et al. ............ 504/142 |
| 5,078,782 A | 1/1992 | Nielsen et al. | |
| 5,093,124 A | 3/1992 | Kulenkampff | |
| 5,106,410 A * | 4/1992 | Puritch et al. ............ 504/142 |
| 5,123,950 A | 6/1992 | Homma et al. | |
| 5,143,718 A * | 9/1992 | Bar-Shalom ............ 424/47 |
| 5,246,716 A * | 9/1993 | Sedun et al. ............ 424/713 |
| 5,248,694 A | 9/1993 | Homma et al. | |
| 5,366,995 A * | 11/1994 | Savage et al. ............ 514/558 |
| 5,496,568 A | 3/1996 | Winston | |
| 5,518,986 A | 5/1996 | Winston | |
| 5,518,987 A | 5/1996 | Winston | |
| 5,741,502 A * | 4/1998 | Roberts ............ 424/405 |
| 5,756,128 A | 5/1998 | Arimoto | |
| 5,849,663 A | 12/1998 | Hasebe et al. | |
| 5,863,909 A | 1/1999 | Kurita et al. | |
| 5,998,358 A * | 12/1999 | Herdt et al. ............ 510/506 |
| 6,008,158 A | 12/1999 | Hasebe et al. | |
| 6,039,966 A | 3/2000 | Kostka et al. | |
| 6,180,566 B1 | 1/2001 | Nielsen et al. | |
| 6,218,336 B1 | 4/2001 | Coleman | |
| 6,291,401 B1 | 9/2001 | DuFau et al. | |
| 6,509,297 B1 | 1/2003 | Coleman | |
| 2003/0224938 A1 | 12/2003 | Coleman | |

FOREIGN PATENT DOCUMENTS

| | | | |
|---|---|---|---|
| SU | 0844584 | | 7/1981 |
| WO | WO 91/13552 | * | 9/1991 |

* cited by examiner

*Primary Examiner*—Johann R Richter
*Assistant Examiner*—Mei-Ping Chui
(74) *Attorney, Agent, or Firm*—Edward E. Sowers; Brannon & Sowers PC

(57) ABSTRACT

This invention relates to agricultural compositions that find particular use as a fungicide composition. The fungicide composition can include one or more fatty acids and one or more organic acids different from the fatty acid. The organic acid can but need not exhibit any fungicidal activity; however, when combined with a fatty acid, the organic acid functions as a potent synergist for the fatty acid as a fungicide. Additionally, the fungicide composition can include other components such as emulsifiers, adjuvants, surfactants and diluents. The fungicide composition significantly reduces or prevents the fungal infection of cash crops including vegetables, fruits, berries, seeds, grains and at higher application rates, can also be used as a harvest aid or desiccant for harvested crops such as potatoes.

32 Claims, No Drawings

FUNGICIDE COMPOSITIONS

CROSS REFERENCE TO RELATED APPLICATIONS

The present application claims the benefit of U.S. Provisional Application Ser. No. 60/347,208 filed on Jan. 9, 2002, which is hereby incorporated by reference in its entirety.

BACKGROUND OF THE INVENTION

The present invention relates to compositions and methods for treating plants and agricultural products.

Fungus can often attack and destroy crops and, if not kill them, can induce distress in the crops so that they succumb to other diseases and/or significantly lower crop yield. Furthermore, agricultural products can be particularly susceptible to damage by fungus after the products are harvested. Many of the products are stored for extended periods of time before they reach the consumer or are used by the consumer. The fungus can make the harvested agricultural products inedible or otherwise unusable. This can be particularly problematic since a significant amount of effort and money has gone into producing and harvesting the agricultural products; all of this can be lost before the products reach the consumer.

Consequently, it is not surprising that there are many fungicide compositions currently on the market. However, there is a growing concern that some of these compositions, one or more of their components, and/or metabolites eventually find their way into the food sources for animals, including humans. Unfortunately, many fungicides and/or their byproducts are moderately and even extremely toxic. Further, some fungicides are suspected or known carcinogens. Despite this fact, many fungicides continue to be used and are needed to protect cash crops. It is important to note that some fungi are themselves extremely toxic or produce toxic components. For example, aflatoxins belong to a class of fungal metabolites and are known to occur naturally in many products including peanuts, cottonseed, corn, peppers, etc. Many aflatoxins are extremely toxic and some are listed as known carcinogens. Consequently, fungicides are needed to protect and preserve agricultural products and ensure the public's health.

Consequently, with increased demand and necessity for agricultural products to feed and clothe the world population, and with the risks associated with eating and using diseased products, there is an increased need in the field for advancements. These advancements include improved methods and compositions for treating plants, particularly cash crops and products derived from the plants. The present invention is such an advancement and provides a wide variety of benefits and advantages.

SUMMARY OF THE INVENTION

The present invention relates to novel agricultural compositions and use thereof. Various aspects of the invention are novel, non-obvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a composition comprising a combination of a fatty acid species or a salt thereof, and an organic acid species or a salt thereof, different from the fatty acid and its salts. In preferred embodiments, the composition also includes a wide variety of additives including one or more of emulsifiers, adjuvants, diluents, dispersants, and/or surfactants, to name just a few.

In another form, the present invention provides a fungicide composition comprising a fatty acid, or salt thereof, having between 5 and 22 carbon included in a fungicidally-effective amount and an organic carboxylic acid, or a salt thereof, that is different from the fatty acid. The fatty acid is an unsubstituted aliphatic carboxylic acid. The organic carboxylic acid has between 1 and 12 carbons and is substituted with one or more substituents selected from the group consisting of: hydroxyl, halide, oxygen, nitrogen, amine, sulfur, phosphate, carboxyl. The composition also can include a carrier and additives as listed above.

The fungicide can be formulated as a liquid concentrate that can be diluted with water to yield a ready-to-use formulation suitable for application to the locus of plants, their fruit, vegetable, seeds and/or nuts. The concentrate or the ready-to-use formulation can be supplied as an aqueous solution, a suspension, or an emulsion. The concentrate or the ready-to-use formulation can include additional components and be specifically formulated to target either a particular plant species crop and/or a particular pathogen.

In selected embodiments, the fatty acid species can be selected as a fatty monocarboxylic acid, having between 5 and 22 carbons. The fatty acid species can be saturated or unsaturated. The organic acid species can be selected from a wide variety of organic acids including monocarboxylic acids having between 1 and 12 carbon atoms which carbon atoms can be substituted with one or more of hydroxyl, halide, oxygen and nitrogen, or hydroxyl, halide, oxygen, nitrogen, amine, sulfur, phosphate, carboxyl substituents.

In still yet another form, the present invention provides a method of controlling fungus, said method comprising contacting one or more of plants, fruit, vegetables, seeds, and nuts with an effective amount of a ready-to-use composition prepared by diluting with water the concentrate listed above.

In still yet another form, the present invention provides a method of treating a crop product, said method comprising applying to the crop product a fungicidal composition comprising a fungicidally active amount of a fatty acid, having between 5 and 22 carbon atoms and an organic acid different from the fatty acid. In still another form of this method, the present invention further involves a method of treatment comprising identifying a crop product susceptible to fungal infection and applying the fungicidal composition to the crop product in one or more treatments.

DETAILED DESCRIPTION OF THE INVENTION

For the purposes of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described compositions, methods, or systems, and any further applications of the principles of the invention as described herein, are contemplated as would normally occur to one skilled in the art to which the invention relates.

In general, the present invention is directed to an agricultural composition particularly useful for treating plants under cultivation, agricultural products, produce, grains, cash crops, or other stable crops. The present composition finds particularly useful advantages as a fungicide. The agricultural composition can include one or more fatty acids in combination with one or more organic acids, that is/are different from the fatty acid(s). The composition can be provided either as a liquid concentrate or a ready-to-use formulation. Either the liquid concentrate or the ready-to-use formulation can be a clear, aqueous solution, a suspension, or an emulsion.

In particularly preferred embodiments, the agricultural composition includes additional components such as emulsifiers, diluents, adjuvants, dispersants, and/or surfactants. The agricultural composition can be applied to the locus of plants and/or to the agricultural products. For example, the agricultural composition can be applied either as a pre-emergent, post-emergent, foliar or post-harvest application. Additionally, the composition can be applied to agricultural products or crop products such as fruits, nuts, berries, vegetables, grains, seeds, stems, bark, leaves, or any other component derived from the plant either before or after harvesting the products. When applied to an agricultural product, the composition can be provided either as a spray or a dipped solution and can be used as a single or multiple treatment application. The agricultural composition can be used and applied prophylactically or to treat an emerging or existing fungicide infection.

The agricultural composition can include one or more fatty acids. The fatty acid can be selected from a wide variety of fatty acids commercially available and/or widely known to those skilled in the art. In preferred embodiments, the fatty acid is selected to prevent, inhibit and/or retard fungal infections or fungal growth on plants. The fatty acids are aliphatic hydrocarbons with a terminal carboxylic acid functionality. Preferred examples of fatty acids include aliphatic, saturated, or unsaturated monocarboxylic fatty acids having between 5 and 22 carbon atoms. More preferably, the fatty acids are selected to have between 7 and 10 carbon atoms.

Preferably, fatty acids are selected that prevent, inhibit and/or retard fungal infections. Retardation or inhibition of fungal infections can be determined by a variety of commonly known evaluations. For example, the growth rate of fungi, measured in surface area of plant leaves or stems, can be measured and monitored over time. Consequently, it has been determined that certain fatty acids prevent, inhibit/retard fungal infections better than other fatty acids. Not to be limiting in any manner, it has been determined, for example, that fatty acids having 8 carbon atoms inhibit *Botrytis cinerea* on raspberries better than acids having 7 carbon atoms, which are better than acids having 9 carbon atoms, which are better than acids having 10 carbon atoms, all of which are better than acids having 6 carbon atoms.

Specific examples of available fatty acids for use in the present invention include pentanoic, hexanoic, heptanoic acid (enanthic acid), octanoic acid (caprylic acid), nonanoic acid (pelargonic acid), decanoic acid (n-capric acid), undecanoic acid, lauric acid, myristic acid, palmitic acid, stearic acid, oleic acid, linolenic acid, linoleic acid, erucic acid, palmitoleic acid, pentadecanoic acid, margaric acid, arachidic acid, arachidonic acid, behenic acid, and soya fatty acids, 2-hexyldecanoic acid, and the like.

The fatty acid is included in the agricultural composition in a desired amount; preferably in a fungicidally effective amount sufficient to elicit prevention or inhibition of fungal growth. In preferred embodiments, a concentrated formulation of the agricultural composition comprises between about 1% v/v and about 99% v/v of a fatty acid; more preferably, between about 50 and about 90% v/v based upon the total volume of the concentrated formulation.

The agricultural composition also includes an organic acid that is different from the fatty acid. The organic acid can be selected from a wide variety of known and commonly used acids. The organic acid, in combination with one or more fatty acid(s) in the fungicidal composition, promotes additional or a synergistic fungicidal activity over that exhibited by the fatty acid(s) used individually or with one of the other additives. The organic acid can be selected to include acids having between 2 and 20 carbon atoms. The organic acids can be selected to be an aliphatic, saturated or unsaturated, cyclic, and/or aromatic. The acids can be mono acids, diacids, triacids, ketoacids, sugar acids, or hydroxy acids, each of which can be substituted with one or more oxygen, hydroxy groups, nitrogen, halide, or hydroxyl, halide, oxygen and nitrogen, or hydroxyl, halide, oxygen, nitrogen, amine, sulfur, phosphate, carboxyl substituents.

Specific examples of readily available organic acids for use in the present invention include but are not limited to mevalonic acid, glycolic acid, ketoglutaric acid, glutaric acid, glyceric acid, malonic acid, benzoic acid, trichloroacetic acid, pyruvic acid, cinnamic acid, formic acid, fumaric acid, isocitric acid, oxalacetic acid, acrylic acid, isobutyric acid, itaconic acid, humic acid, tetrahydrofurfuryl salicylic acid, diethylamine salicylic acid, fulvic acids, and sugar acids such as pentonic acid (i.e., ribonic acid and xylonic acid), hexonic acid (i.e., gluconic acid and galactonic acid), and bionic acids (i.e., saccharic acid and ascorbic acid), alanine, glycine, isoleucine, leucine, methionine, phenylalanine, proline, tryptophan, valine, asparagine, cysteine, glutamine, serine, threonine, tyrosine, aspartic acid, glutamic acid, arginine, histidine and lysine and mixtures of these acids.

A "ready-to-use formulation" of the agricultural composition (a concentrated formulation that is diluted in water or other diluent such as seed oil, ethanol, etc.) can include the organic acid species together with one or more fatty acid(s) in an amount sufficient to induce prevention, inhibition or retardation of fungal infection and comprises an amount of the fatty and organic acids less than the amount that will inhibit plant growth. In preferred embodiments, a ready-to-use formulation for use in the present invention comprises at least about 0.001% v/v, of fatty and organic acids; more preferably at least about 0.05% v/v; and still yet more preferably at least about 0.01% % v/v of the fatty acid and organic acid, based upon the total volume of the formulation.

The agricultural composition can include both the fatty acids species and the organic acid species, different from the fatty acid species in a wide range of ratios. In preferred embodiments, the ratio of fatty acid species to organic acids species is in a weight ratio of between 1:1000 to about 1000:1. More preferably, the weight ratio of fatty acid species to organic acid species is between about 1:5 to about 5:1. The agricultural composition for use in the present invention can be prepared by admixing all desired ingredients at the same time.

Alternatively, the fatty acid species can be premixed with one or more additives such as an adjuvants, surfactants, emulsifiers, and/or diluents in water. When premixed, the ratio of fatty acid to additive(s) can be between about 1:5 to about 1000:1. The fatty acid and additive(s), either singly or as a combined pre-mix, can be suitably dissolved in a solvent such as water, alcohol, and/or an organic solvent, such as an oil or ketone, suitable for treatment of agricultural products or plants.

In preferred embodiments, either the concentrate or the ready-to-use formulation is admixed with a variety of additives; for example, adjuvants, surfactants, emulsifiers, and/or diluents. The additive can be selected from a wide variety of known commercially available products. Typical adjuvants, surfactants, and/or emulsifiers for use with fatty acids include any synthetic or natural emulsifier including for example: organosilicones (i.e., Sylgard 309 sold by Dow Corning Corp, Kinetic, Silwet L77), methylated seed oil, and ethylated seed oil (i.e., Scoil sold by Agsco or Hasten sold by Wilfarm), alkylpolyoxyethylene ethers (i.e., Activator 90), alkylarylalolates (i.e., APSA 20), alkylphenol ethoxylate and alcohol alkoxylate surfactants (i.e., products sold by Huntsman), fatty acid and fatty amine ethoxylates (i.e., products sold by Huntsman), anionic surfactants such as sulfosuccinates, sulfonates, and phosphate esters (products sold by Huntsman), polyethylene glycol (PEG) fatty acid esters and alkyl napthalene sulfonates (i.e., products sold by Adjuvants Unlimited), tristyrylphenol, castor, oil and fatty amine ethoxylates and products sold by Cognis such as sorbitan and ethoxylated sorbitan esters, ethoxylated alcohols and alkylphenols, ethoxylated vegetable oils, alkyl, glycol and glycerol esters. Also to be included are natural emulsifiers such as lecithin. Examples of diluents include mineral oil and natural oils such as vegetable oil, coconut oil, olive oil, corn oil, canola oil, cottonseed oil, and soybean oil, to name just a few.

In selected embodiments, a "ready-to-use formulation" (i.e., a concentrated formulation diluted in water or other solvent) according to the present invention contains between about 0.001% v/v and about 3% v/v fatty acid, more preferably between about 0.005% v/v and about 2.0% v/v of the fatty acid, still more preferably between about 0.01% v/v and about 1.0% v/v of the fatty acid. The organic acid is included in an amount between about 0.001% v/v and about 4% v/v; more preferably, between about 0.1% v/v and about 1% v/v (or wt/vol, for solid organic acids). When used as a foliar spray application treatment, the fungicide composition can be directly applied to the crop products; i.e., leaves, fruit or other crops, such as fruit, vegetables, berries, nuts, seeds, and the like. Furthermore, in use, the fungicide composition can be applied as a single use or single treatment, or in multiple treatments.

In other embodiments, the fungicide composition can be combined with one or more other treatment processes and compositions. For example, the fungicide composition can be combined with a herbicide composition, a desiccant composition, or an insecticide composition. A combination of the fungicide with one or more other treatment compositions and applications obviously reduces treatment costs and consequently can improve efficiency of operation.

In preferred embodiments, the selected combination of a fatty acid species and an organic acid species exhibits unexpected results or synergism by providing improved fungicidal activity over any of the individual components by themselves. The organic acid, alone, has little or no fungicidal activity; however, when combined with the fatty acid, a strong synergism results.

The crop products can be selected from any commonly known or used cash crops including fruits, vegetables, berries, nuts, leaves, seeds, grains and the like.

Specific examples in which the fungicide composition finds particular use include crops, strawberries, raspberries, blueberries, melons, stone fruit, nut crops, potatoes, vegetables, turf grasses, seed crops (i.e., seed grasses, alfalfa seed), corn, rice, wheat, soybeans, dry beans, peanuts, cotton, sorghum, and other row crops, curcurbits, other small fruit crops, and horticultural plants.

The fungicide composition can be provided to the end user either as a liquid concentrate or in a "ready-to-use composition" (i.e., a concentrated formulation diluted in water or other diluent). When provided as a liquid concentrate, the fungicide composition includes the fatty acid species in a range, of between about 1% v/v and about 99% v/v, the organic acid species in a range between about 0.1% v/v and about 90% v/v, and the additives in a range between about 0.01% v/v and about 80% v/v.

In another embodiment, the fungicide composition can be provided as: (a) a harvest aid to desiccate foliage, stems, and/or vines prior to harvest crops such as seed grasses, onions, potatoes, cotton, and dry beans, or (b) a preservative to treat and/or preserve the harvested crops such as fruits, vegetables, berries, nuts, leaves, seeds, grains, and the like. When provided as a preservative, the fungicide composition can be applied either as a spray or as a dip solution. When provided as a dip solution, the fungicide composition can be used in a large vat in which the harvested crop is dipped into the liquid composition. Thereafter, the submerged crop is removed from the fungicide composition and allowed to drain followed by drying. The dried product can then be safely stored for use at a later time. Furthermore, when used as a preservative, the fungicide composition can be used immediately after harvest or at any time subsequent to harvesting.

The fungicide composition exhibits a broad range of fungicide activity against a large number of target pathogens. Non-limiting examples of specific pathogens targeted by the fungicide composition include: *Botrytis cinerea* (i.e., *Botrytis* bunch rot, gray mold, *Botrytis* blight), *Phomopsis viticola* (i.e., *Phomopsis* cane and leaf spot), *Phomopsis rachis*, *Phomopsis vaccinii* (i.e., *Phomopsis* twigblight and canker), downy mildew, *Sphaerotheca macularis* (i.e., powdery mildew), *Guignardia bidwellii* (i.e., black rot), *Monilinia vacinii-cormbosi* (i.e., mummy berry), *Phragmidium* sp. (i.e., yellow rust), *Drepanopeziza* sp. (i.e., anthracnose), *Kuehneola* sp. (i.e., cane and leaf rust), *Sphaerulina* sp. (i.e., orange rust), *Arthuriomyces* sp. (i.e., powder mildew), *Mycosphaerella* sp. (leaf spot), *Colletotrichum acutatum* (i.e., anthracnose fruit rot), *Verticillium albo-atrum* (i.e., *Verticillium* wilt), *Phytophthora fragariae* (i.e., red stele root rot), *Dendrophoma obscurans* (i.e., stem end rot, leaf blight), *Phytophthora cactorum* (i.e., leather rot), *Diplocarpon earliana* (i.e., leaf scorch), *Godronia cassandrac* (i.e., fusicoccum canker), *Alternaria* sp. (i.e., *Alternaria* fruit rot), *Exobasidium vaccinii* (i.e., red leaf disease), *Microsphaera vaccinii* (i.e., powdery mildew), *Venturia inaegualis* (i.e., apple scab), *Gymnosporangium* sp. (i.e., apple rust), *Podosphaera leucotricha* (i.e., apple powdery mildew), black rot of apple, blossom end rot of apple, blue mold of apple, brown rot of stone fruit, *Rhizopus* sp., *Leucostoma cincta* or *Leucostoma persoonii* (i.e., *cytospora* canker of stone fruits), white rot of apple, *Monilinia fructicola* (i.e., brown rot of stone fruit), *Blumeriella jaapii* (i.e., cherry leaf spot of stone fruit), sooty mold of pear, pear leafspot, pear leaf blight and fruit spot, *Pythium ultimatum*, *Phytophthora infestans* (late blight, potatoes), *Aspergillus* sp. (i.e., *Aspergillus paraciticus*), *Apiosporina morbosa* (i.e., black knot of stone fruit), *Rhizoctonia solani* (i.e., black scurf in potatoes, aerial blight, soybeans), *Alternaria solani* (early blight, potatoes), *Sclerotium rolfsii* (i.e., *Sclerotium* rot, sugar beets), *Fusarium* sp., *Septoria* sp. and white mold in soybeans and the like.

For the purpose of promoting further understanding and appreciation of the present invention and its advantages, the following examples are provided. It will be understood, however, that these examples are illustrative and not limiting in any fashion. Unless specifically indicated to the contrary, all percentages listed below in the following examples are percentage by volume, based upon the total volume of the resulting composition.

EXAMPLE 1

Retardation of White Mold Growth on Soybean Foliage

Soybean foliage was treated with caprylic acid with a solution that contains sorbitan monolaurate, sold under the trade name Emsorb 6915 by Cognis, and mineral oil. A stock solution of the caprylic acid was formulated to include about 0.75% caprylic acid, about 1% HASTEN (or 0.5% Sylgard 309), about 0.21% sorbitan monolaurate, and about 0.11% mineral oil by volume percent. This was applied to plants at 40 gallons per acre (gpa). The plants were about 9-12 inches in height. Foliage from the plants was collected at days 2, 4, 7, and 34 after fungicide treatment, washed in warm water, drained, and then inoculated with the mold inoculum. White mold inoculum (5 mm diameter plugs) was used to infect the foliage of soybean plants (species GL2415). The inoculated foliage was incubated for 2-3 days at room temperature (at 100% humidity) under fluorescent lighting. The results are listed below in Table 1.

TABLE 1

| Treatment Solution | Average radii of fungal growth[1] at days after fungicide treatment: | | | |
|---|---|---|---|---|
| | 2 | 4 | 7 | 34 |
| Control (untreated) | 100 | 100 | 100 | 100 |
| 0.21% 6915 + 0.11% mineral oil + 0.75% caprylic acid + 1% HASTEN | 50 | 44 | 52 | * |
| 0.29% 6915 + 0.14% mineral oil + 1% caprylic acid + 1% HASTEN | 55 | 45 | 35 | * |
| 0.21% 6915 + 0.11% mineral oil + 0.75% caprylic acid + 0.5% SYLGARD | 46 | 47 | 26 | 66 |
| 0.29% 6915 + 0.14% mineral oil + 1% caprylic acid + 0.5% SYLGARD | 53 | 29 | 38 | 67 |

[1]Fungal growth for Control (treatment 1) is expressed as 100%.

From the results listed above, it can be determined that even as little as 0.75% caprylic acid demonstrated significant reduction in the fungal growth on soybean foliage.

EXAMPLE 2

Retardation of White Mold Growth on Soybean Foliage

The foliar treatments were applied at a rate of 40 gpa (40 psi) to 4 soybean plants (15-20" in height) per each treatment group (Table 2). Two leafs/plant were used for the detached leaf assay. White mold inoculums (5 mm plugs from potato dextrose agar plates) were used to inoculate soybean foliage (species GL 2415). Foliage from the soybean plants were washed in warm water, drained, collected and inoculated, and the inoculated foliage was incubated for 3 days at room temperature (100% humidity) under fluorescent lighting. The results are listed in Table 2 below.

TABLE 2

| Treatment Solution | Average Radii (mm)[2] | Percent Fungal Growth Based on Control |
|---|---|---|
| Control (untreated) | 3.14 | 100% |
| 0.21% 6915[1] + 0.11% mineral oil | 3.012 | 96 |
| 0.2% 6915[1] + 0.11% mineral oil + 0.75% caprylic acid | 2.225 | 71 |
| 0.07% 6915[1] + 0.04% mineral oil + 0.25% caprylic acid | 2.75 | 88 |
| 0.02% 6915[1] + 0.01% mineral oil + 0.08% caprylic acid | 2.813 | 90 |

[1]Cognis Emsorb 6915
[2]Average radii (mm) of fungal growth on leaf surface measured at day 3

From the results listed in Table 2 it can be demonstrated that caprylic acid significantly inhibits the fungal growth of white mold on soybean foliage. The orthogonal comparison of the control 1 and treatment solution 3 was statistically significant at P>0.95, and orthogonal comparison of treatment solution 2 versus treatment solution 3 indicated that treatment 3 was statistically significant at P>0.90.

EXAMPLE 3

Reduction of *Phytophthora Infestans* on Potato Foliage at 1 and 10 Days After Treatment Snowden potatoes were grown in Baccto potting soil to a height of 14-21 inches. All plants were fertilized one time per week. The plants were then treated as listed below in Table 3. The treatment solutions listed below in Table 3 were applied at 40 gpa (40 psi) to three plants (3 plants per treatment group). Each treatment included 0.2% SYLGARD 309 sold by Dow Corning. At one and ten days after treatment, foliage (4 leafs per plant) were washed in warm water, drained and inoculated. The inoculated foliage was incubated for 2-3 days at room temperature (100% humidity) via fluorescent lighting. *P. infestans* plugs from PDA plates were used to inoculate 4 leaves/plant. The results are listed below in Table 3.

TABLE 3

| Treatment Solution | Average radii (mm) of Growth (*P. infestans*) | | | |
|---|---|---|---|---|
| | Day 1 | | Day 10 | |
| 1. 0.57% 6915[1] + 0.29% mineral oil | 9.49 | 100% | 8.35 | 100% |
| 0.57% 6915[1] + 0.29% mineral oil + 2% caprylic acid | 1.24 | 13%[2] | 1.35 | 16%[3] |

[1]Cognis Emsorb 6915
[2]Based upon the control at Day 1 after application of treatments
[3]Based upon the control at Day 10 after application of treatments From the results listed above in Table 3, it can be determined that a solution containing 2% caprylic acid significantly inhibits the growth of *Phytophthora infestans* on potato foliage. The treatment solution 2 was significantly different from the treatment 1 for disease control as determined via an ANOVA statistical test (P>0.95).

EXAMPLE 4

Inhibition of Fungus Infection on Strawberries

A field of strawberries (Northeaster variety) was partitioned into four separate areas. Strawberries were harvested from the four separated areas. For each treatment group, berries were randomly selected from the four separate areas. Berries were submersed for 60 seconds in the specified treatment solution listed below in Table 4. After 60 seconds, the berries were removed from the solution, briefly drained, and incubated at room temperature on a screen suspended above water in a sealed chamber. The infected berries were analyzed to determine the host fungi. The primary host fungi were *Botrytis cinerea*, and the secondary fungi were *Rhizopus*. The results are listed below in Table 4.

TABLE 4

| | | Infected berries (% of total) determined at The specified days after treatment (DAT) | | | | |
|---|---|---|---|---|---|---|
| Group | Treatment Solution | Day 3 | Day 4 | Day 5 | Day 6 | Day 7 |
| 1. | Water | 70% | 85% | 100% | 100% | 100% |
| 2. | 0.35% glycolic acid | 75% | 90% | 100% | 100% | 100% |
| 3. | 0.35% glycolic acid and 0.35% caprylic/0.1% 6915[1]/0.05% mineral oil | 5% | 15% | 20% | 30% | 40% |
| 4. | 0.35% caprylic acid/0.1% 6915[2]/0.05% mineral oil | 25% | 50% | 60% | 65% | 75% |

[1]Cognis Emsorb 6915

It can be determined from analyzing the results listed above in Table 4 that caprylic acid (treatment #4) exhibits a significant inhibition of fungus infection. However, it is also determined that the combination of glycolic acid and caprylic acid (treatment #3) provide unexpected and synergistic inhibition of fungal infection of strawberries. No inhibition is found when only glycolic acid is used.

EXAMPLE 5

Inhibition of Fungus Infection on Strawberries

Strawberries described and treated as above in Example 4, with the solutions shown below in Table 5.

TABLE 5

| | | Infected berries (% of total) on days after treatment | | |
|---|---|---|---|---|
| Group | Treatment Solutions | Day 2 | Day 3 | Day 4 |
| 1. | Water | 75% | 90% | 100% |
| 2. | 0.35% glycolic acid | 70% | 95% | 100% |
| 3. | 0.35% glycolic acid + 0.70% caprylic acid/0.20% 6915[2]/0.10% mineral oil | 0% | 0% | 5% |

TABLE 5-continued

| | | Infected berries (% of total) on days after treatment | | |
|---|---|---|---|---|
| Group | Treatment Solutions | Day 2 | Day 3 | Day 4 |
| 4 | 0.70% caprylic acid/0.20% 6915[1]/0.10% mineral oil | 25% | 60% | 95% |

[1]Cognis Emsorb 6915

The data demonstrate the synergist fungicidal activity of caprylic and glycolic acids.

EXAMPLE 6

Inhibition of Fungal Infections on Strawberries: Comparison of Various Organic Acids as Synergists with Caprylic Acid Strawberries (Northeastern) were selected and treated as described above in Example 5 with the solutions listed below in Table 6. The predominant fungal infection was *Botrytis cinerea* and the secondary infection was *Rhizopus*.

TABLE 6

| | | Infected berries (% of total treated berries): days after treatments # 1-7 | | | | |
|---|---|---|---|---|---|---|
| Group | Treatment Solution | Day 2 | Day 3 | Day 5 | Day 7 | Day 9 |
| 1. | Water | 60% | 75% | 95% | 95% | 95% |
| 2. | 0.7% caprylic acid/0.2% 6915[1]/0.1% mineral oil | 5% | 25% | 55% | 75% | 80% |
| 3. | 0.7% caprylic acid/0.2% 6915[1]/0.1% mineral oil and 0.35% glycolic acid | 0% | 0% | 0% | 0% | 5% |
| 4. | 0.7% caprylic acid/0.2% 6915[1]/0.1% mineral oil and 0.35% potassium sorbate | 0% | 0% | 15% | 25% | 30% |

[1]Cognis Emsorb 6915

For Northeastern strawberries, glycolic acid in combination with caprylic acid exhibited unexpectedly high anti-fungal properties and was the best treatment under the test conditions.

EXAMPLE 7

Inhibition of Fungus Infections on Raspberries

Raspberries (Tulamen variety) harvested from four separate plots were divided into three groups, each group of harvested berries were submerged for 60 seconds in the appropriate solution listed below in Table 7, briefly drained and dried and then incubated at room temperature on a screen suspended above water in a sealed chamber. The predominant infection observed on the raspberries was *Botrytis cinerea* and the secondary infection was *Cladosporium*. The results are listed below in Table 7.

TABLE 7

| | | Infected berries (% of total) on days after treatment | | | |
|---|---|---|---|---|---|
| Group | Treatment Solution | Day 2 | Day 3 | Day 4 | Day 5 |
| 1. | Water | 61% | 85% | 96% | 96% |
| 2. | 0.7% caprylic acid/0.2% | 0% | 0% | 0% | 0% |

TABLE 7-continued

| | | Infected berries (% of total) on days after treatment | | | |
|---|---|---|---|---|---|
| Group | Treatment Solution | Day 2 | Day 3 | Day 4 | Day 5 |
| 3. | 6915[1]/0.1% mineral oil + 0.5% glycolic acid 0.7% caprylic acid/ 0.12% oleic acid/0.01% Leciprime | 0% | 0% | 0% | 0% |

[1]Cognis Emsorb 6915

EXAMPLE 8

Inhibition of Fungal Growth by Caprylic Acid and Glycolic Acid

Potato dextrose agar (PDA) plates, +/−amendments (treatments #1-6, Table 8), were inoculated with *Septoria*, late blight or white mold. There were four replicate plates/treatment group/fungus type. After incubation of the plates at room temperature (three days), fungal growth was measured.

TABLE 8

| | | Measurement of fungal growth on day 2 or 3 after inoculum[4] | | | | | |
|---|---|---|---|---|---|---|---|
| | | Septoria | | Late blight | | White mold | |
| Group | Amendments in PDA Plates | Day 2 | Day 3 | Day 2 | Day 3 | Day 2 | Day 3 |
| 1. | 0.0175% C-8[1]/0.005% 6915/ 0.003% mineral oil | 92 | 94 | 82 | 93 | 24 | 52 |
| 2. | 0.0175% C-8[1]/0.005% 6915/ 0.003% mineral oil and 0.0175% glycolic acid | 60 | 69 | 65 | 78 | 41 | 65 |
| 3. | 0.07% C-8[1]/0.02% 6915[2]/0.01% mineral oil | 0 | 19 | 10 | 25 | 0 | 0 |
| 4. | 0.07% C-8[1]/0.02% 6915[2]/0.01% mineral oil and 0.0175% glycolic acid[3] | 0 | 2 | 0 | 10 | 0 | 0 |
| 5. | 0.0175% glycolic acid[3] | 80 | 90 | 79 | 104 | 127 | 108 |
| 6. | no amendments | 100 | 100 | 100 | 100 | 100 | 100 |

[1]C-8 stock solution: = 70% caprylic acid/20% 6915/10% mineral oil
[2]Cognis Emsorb 6915 (sorbitan monolaurate)
[3]Glycolic acid = DuPont 70% glycolic acid
[4]Based on fungal growth on the control plate (100%)
Addition of glycolic acid enhanced fungicidal activity of caprylic acid (C8).

EXAMPLE 9

Inhibitions of Fungal Infections on Fresh Raspberries

Raspberries (Heritage variety) were harvested from four plots. Nine berries per plot (4 plots) were used for each treatment group. The berries were randomly divided into seven (7) groups. Each group of the harvested berries were submersed for 60 seconds in the appropriate solution listed below in Table 9. Thereafter the berries were removed from the solution, briefly drained and incubated at room temperature on a screen suspended above water in a sealed chamber. The predominant infection for the berries was determined to be *Botrytis cinerea*. The results are listed below in Table 9.

TABLE 9

| | | Infected berries (% of total) on days after treatment | | | | | | |
|---|---|---|---|---|---|---|---|---|
| Group | Treatment Solution | Day 2 | Day 3 | Day 4 | Day 6 | Day 8 | Day 10 | Day 12 |
| 1. | Water | 33% | 83% | 89% | 89% | 89% | 92% | 92% |
| 2. | 0.525% caprylic acid/ 0.15% 6915[1]/0.075% mineral oil | 0 | 0 | 11% | 17% | 44% | 67% | 67% |
| 3. | 0.75% tartaric acid | 31% | 58% | 86% | 92% | 92% | 92% | 92% |
| 4. | 0.525% caprylic acid/0.087% oleic acid/0.009% Leciprime[2] | 0 | 0 | 0 | 3% | 3% | 3% | 8% |
| 5. | 0.263% caprylic acid/0.044% oleic acid/0.005% Leciprime[2] | 0 | 0 | 0 | 6% | 14% | 25% | 33% |
| 6. | 0.131% caprylic acid/0.022% oleic acid/0.002% Leciprime[2] | 3% | 8% | 11% | 14% | 25% | 28% | 28% |

[1]Cognis Emsorb 6915 (sorbitan monolaurate)
[2]Leciprime is a lecithin product

EXAMPLE 10

Inhibitions of Fungal Infections on Fresh Raspberries: Comparison of Various Fatty Acid Species (C6-C10) as Fungicide Active Ingredients Raspberries (Heritage variety) were harvested and treated as described above in Example 9. The results of the treatments for various saturated fatty acids are listed below in Table 10.

TABLE 10

| | | Infected berries (% of total) on days after treatment | | | | | | |
|---|---|---|---|---|---|---|---|---|
| Group | Treatment Solutions | Day 1 | Day 2 | Day 3 | Day 5 | Day 7 | Day 9 | Day 11 |
| 1. | Water | 19% | 58% | 92% | 97% | 97% | 97% | 97% |
| 2. | 0.1% 6915[1]/0.05% mineral oil/0.35% caproic acid | 3% | 39% | 75% | 97% | 97% | 97% | 100% |
| 3. | 0.1% 6915/0.05% mineral oil/0.35% heptanoic acid | 0% | 0% | 6% | 44% | 69% | 83% | 89% |
| 4. | 0.1% 6915/0.05% mineral oil/0.35% caprylic acid | 0% | 0% | 3% | 25% | 53% | 67% | 78% |
| 5. | 0.1% 6915/0.05% mineral oil/0.35% pelargonic acid | 0% | 3% | 14% | 68% | 89% | 92% | 97% |
| 6. | 0.1% 6915/0.05% mineral oil/0.35% capric acid | 0% | 31% | 69% | 97% | 100% | 100% | 100% |

[1]Cognis Emsorb 6915 (sorbitan monolaurate)

The above data indicate that the relative fungicidal activity of the fatty acid species against raspberry pathogens was: caprylic>heptanoic>pelargonic>capric>caproic acid.

EXAMPLE 11

Effects of Fungicide Formulation on Greenhouse Soybean Production

Five (5) groups of soybean plants (variety GL 2415) were grown to a height of 15-20 inches and then each group was treated with the indicated solutions listed below in Table 11. Each plant was treated with a solution at an application rate of 40 gpa at (40 psi). After treatment, the soybean plants were grown in a greenhouse for 31 days prior to harvest. The results of harvesting are listed below in Table 11.

TABLE 11

| | | Average production/plant[2] | | |
|---|---|---|---|---|
| Group | Treatment Solutions | Bean number | Total bean Weight (grams) | Weight (g) Per bean |
| 1. | Control (untreated) | 16.3 | 18.3 | 1.10 |
| 2. | 0.21% 6915[1] + 0.11% mineral oil | 22.8 | 25.7 | 1.13 |
| 3. | 0.21% 6915[1] + 0.11% mineral oil + 0.75% caprylic acid | 20.8 | 22.5 | 1.10 |
| 4. | 0.07% 6915[1] + 0.04% mineral oil + 0.25% caprylic acid | 21.0 | 24.2 | 1.14 |
| 5. | 0.02% 6915[1] + 0.01% mineral oil + 0.08% caprylic acid | 21.3 | 23.7 | 1.11 |

[1] Cognis Emsorb 6915
[2] Four repetitions (plants) per treatment group.

It can be seen from the data listed in Table 11 above that none of the caprylic acid (C8) treatments adversely affected soybean production. Moreover, there was no phytotoxicity (visual injury) from any of the caprylic acid treatments.

EXAMPLE 12

Efficacy of Selected Formulations Containing Amendment Tetrahydrofurfuryl Salicylate and Huntsman PE 1198 Emulsifier as Inhibitors of Selected Fungal Pathogens Potato dextrose agar (PDA) plates, +/−amendments, were inoculated with selected pathogens. There were several replicate plates used per treatment group (per pathogen tested). After incubation of plates at room temperature, fungal growth was measured.

TABLE 12

| | % inhibition of selected pathogens[1] | | | | | | | | | |
|---|---|---|---|---|---|---|---|---|---|---|
| | 0.015%, v/v of formulations | | | | | 0.100%, v/v of formulations | | | | |
| Treatment Solutions | Late Blight | Alt | Botry | Pyth U. | White Mold | Pestal | Collet | C. paras. | A. Paras. | A. Porric. |
| 1 = 85% pelargonic acid 15% Huntsman PE1198 | 15 | 49 | 30 | 27 | 76 | 85 | 52 | 44 | 66 | 74 |
| 2 = 85% pelargonic acid 7% Huntsman PE 1198 8% tetrahydrofurfuryl salicylate | 27 | 42 | 21 | 33 | 53 | 79 | 41 | 45 | 48 | 79 |
| 3 = 70% caprylic acid 10% Huntsman PE 1198 20% tetrahydrofurfuryl salicylate | 31 | 44 | 42 | 26 | 58 | 88 | 48 | 50 | 50 | 80 |
| 4 = 70% pelargonic acid 10% Huntsman PE 1198 20% tetrahydrofurfuryl salicylate | 23 | 41 | 21 | 32 | 52 | 86 | 47 | 59 | 39 | 77 |
| 5 = 55% pelargonic acid 10% Huntsman PE 1198 35% tetrahydrofurfuryl salicylate | 49 | 44 | 20 | 42 | 39 | 84 | 46 | 68 | 74 | 80 |

TABLE 12-continued

| | % inhibition of selected pathogens[1] | | | | | | | | | |
|---|---|---|---|---|---|---|---|---|---|---|
| | 0.015%, v/v of formulations | | | | | 0.100%, v/v of formulations | | | | |
| Treatment Solutions | Late Blight | Alt | Botry | Pyth U. | White Mold | Pestal | Collet | C. paras. | A. Paras. | A. Porric. |
| 6 = 40% pelargonic acid 10% Huntsman PE 1198 50% tetrahydrofurfuryl salicylate | 77 | 45 | 19 | 44 | 29 | 79 | 53 | 66 | 72 | 82 |

[1]Late blight = Phytophthora
Alt = Alternaria (SWREC)
Botry = Botrytis cinerea (SWREC)
Pyth. U. = Pythium ultimum
Pestal = Pestalotia infestans
Collet = Colletotrichia (SWREC)
C. para = Cylindrocladium parasiticus
A. paras. = Aspergillus parasiticus The average percent inhibition of all pathogens
1=47.7%
2=54.6%
3=56.6%
4=51.7%
5=46.8%
6=51.8%

The combination of tetrahydrofurfuryl salicylate and pelargonic acid exceeded the fungicidal activity of pelargonic acid, alone.

EXAMPLE 13

Synergism Between Caprylic Acid and Organic Acids: Inhibition of *Botrytis cinerea* and White Mold Potato dextrose agar (PDA) plates, +/−amendments, were inoculated with selected pathogens. There were several replicate plates used per treatment group (per pathogen tested). After incubation of plates at room temperature, fungal growth was measured.

TABLE 13

| | Treatment* | Inhibition (%) of Botrytis cinerea | Inhibition (%) of white mold |
|---|---|---|---|
| 1 | 0.014% caprylic acid | 88 | 34 |
| 2 | 0.014% caprylic acid + 0.010% glycolic acid | 98 | 71 |
| 3 | 0.014% caprylic acid + 0.010% diethylamine salicylate | 99 | 93 |
| 4 | 0.010% citric acid | 0 | 0 |
| 5 | 0.010% succinic acid | 0 | 0 |
| 6 | 0.010% glycolic acid | 0 | 0 |
| 7 | 0.010% diethylamine salicylate | 0 | 7 |

Synergy between caprylic acid and each organic acid for white mold
Synergy between caprylic acid and each organic acid for Botrytis
*Treatment formulation: 70% C-8/20% Emsorb 6915/10% mineral oil: 0.020%, v/v, of formulation = 0.0140% C-8 in potato dextrose agar plate Stoichiometric amounts of organic acids used in treatment Combinations of caprylic acid (C8) with organic acids for both pathogens were synergistic.

EXAMPLE 14

Comparison of Low and High Rates of Caprylic Acid Applied to Strawberry and Potato Plant Foliage: Inhibition of *Botrytis cinerea*

The foliage of strawberry plants, (Honeoye variety) and potato plants Snowden variety) were inoculated with fresh *B. cinerea* and incubated at room temperature in moisture chambers for 2-3 days. The inoculated foliage of the plants were then treated with the treatment solutions listed in Table 14 below. It should be noted that no phytotoxicity was observed in any of the treatment solutions.

TABLE 14

| | Treatment Solutions | Inhibition (%) of Botrytis on Potato Foliage | Inhibition (%) of Botrytis on Strawberry Foliage |
|---|---|---|---|
| 1 | Water | 0 | 0 |
| 2 | 0.08% caprylic acid formulation | 15 | 62 |
| 3 | 0.08 caprylic acid formulation + 0.02% glycolic acid | 46 | 53 |
| 4 | 1.5% caprylic acid formulation | 20 | 61 |
| 5 | 1.5% caprylic acid formulation + 0.02% glycolic acid | 46 | 52 |

Actual caprylic acid concentration in treatment #2, 3 was 0.056%

Actual caprylic acid concentration in treatment #4, 5 was 1.050%

Application of treatments at 20 gallons/acre (25 psi)

Foliage inoculated with fresh *B. cinerea* and incubated at room temperature in moisture chambers for 2-3 days Strawberry and potato varieties were Honeoye and Snowden, respectively.

Caprylic acid formulation: 70% caprylic acid/20% Cognis Emsorb 6900/10% mineral oil Glycolic acid (70%) from DuPont No phytotoxicity observed The data indicate that a lower application rate of formulation containing caprylic acid (C8, 0.08%) exhibited a similar fungicidal activity as a higher application rate of the caprylic acid (C8 at 1.5%). Further, formulations containing glycolic acid exhibited enhanced fungicidal activity on potato foliage than similar formulation without the addition of the glycolic acid.

EXAMPLE 15

Inhibition of White Mold on Vista Dry Bean Foliage: Caprylic Acid Formulations Containing Different Adjuvants Experimental details given below in Table 15 illustrate that the addition of tetrahydrofurfuryl salicylate enhanced the fungicidal activity of formulations containing caprylic acid (C8) against white mold.

TABLE 15

| Treatment Solutions | Percent Inhibition of White Mold |
|---|---|
| Water, control | 0 |
| 70% caprylic acid/20% Cognis 6915/10% mineral oil | 61 |
| 51% caprylic acid/39% Cognis 6915/10% high fructose corn syrup | 60 |
| 47% caprylic acid/36% Cognis 6915/17% tetrahydrofurfuryl salicylate | 92 |
| 55% caprylic acid/41% Cognis 6915/4% Exacto 390 | 50 |

Same amount (0.42%) of caprylic acid used in all treatments

All formulations, as concentrated emulsions or diluted in water, were stable; i.e., no phase separation was observed after storage of emulsions for several days. Twelve leaves/treatment group, after treatment, inoculated with white mold from PDA plates. Leaves incubated at 100% humidity for 2 days and zones of infection measured.

No phytotoxicity observed for any of the treatments.

EXAMPLE 16

Inhibition of *Rhizoctonia solani* on Cotton Foliage

The combination of caprylic acid (C8) and tetrahydrofurfuryl salicylate with an emulsifier, PE 1198, was highly effective against *R. solani*.

TABLE 16

| Treatment Solution | Application Rate* | Percent Inhibition of *R. solani* |
|---|---|---|
| Water, control | | 0 |
| 70% caprylic acid/20% PE 1198/10% tetrahydrofurfuryl salicylate | 0.1%, v/v | 89 |
| 70% caprylic acid/20% PE 19198/10% tetrahydrofurfuryl salicylate | 0.2%, v/v | 94 |

*0.1 or 0.2%, v/v, formulation, in water

Foliage dipped in treatment, drained, dried, and inoculated with fresh culture of *Rhizoctonia solani* from PDA plate.

Four leaves from each plant/treatment group inoculated and incubated at 100% humidity for 7 days.

PE 1198 emulsifier from Huntsman

EXAMPLE 17

Comparison of Caprylic Acid and Pelargonic acid as Active Ingredients in Fungicides and Comparison of Emulsifiers Potato dextrose agar (PDA) plates, +/−amendments, were inoculated with selected pathogens. There were several replicate plates used per treatment group (per pathogen tested). After incubation of plates at room temperature, fungal growth was measured.

TABLE 17

| | Treatment Solutions* | % Inhibition of Selected Pathogens by Formulations | | | | | | | |
|---|---|---|---|---|---|---|---|---|---|
| | | *C. para.* | *Alt* | Late Blight | *S. Minor* | *Pyth. U.* | *Botr* | White Mold | Avg |
| 1 | 85% caprylic acid/15% PE 1198 | 7 | 33 | 14 | 83 | 12 | 30 | 68 | 35 |
| 2 | 85% pelargonic acid/15% PE 1198 | 7 | 31 | 25 | 84 | 20 | 25 | 80 | 39 |
| 3 | 85% caprylic acid/15% 6915 | 1 | 11 | 0 | 66 | 7 | 17 | 65 | 24 |
| 4 | 85% pelargonic acid/15% 6915 | 1 | 12 | 0 | 78 | 17 | 13 | 76 | 28 |
| 5 | 85% caprylic acid/15% 6900 | 0 | 10 | 0 | 75 | 5 | 20 | 53 | 23 |
| 6 | 85% caprylic acid/15% 6964 | 0 | 22 | 8 | 85 | 9 | 40 | 65 | 33 |

*0.015%, v/v, formulation used (actual C8 or C9 used was 0.013%)
*C. para* = *Cylindrocladium parasiticus*
*Alt* = *Alternaria*
Late blight = *Phytophtora infestans*
*S. minor* = *Schlerotinia minor*
*Pyth. U.* = *Pythium ultimum*
*Botr* = *Botrytis cinerea*
White mold = *Sclerotinia sclerotiorum*

The data listed in Table 17 above indicate that pelargonic acid exhibited slightly better or same fungicidal activity as caprylic acid against a wide variety of fungi (PDA plate assay). Further the emulsifier, PE 1198, provided better results than other comparable emulsifiers.

EXAMPLE 18

Comparison of Caprylic Acid (C8) and Pelargonic acid (C9) +/−stoichiometric amounts of organic acid amendments.

Potato dextrose agar (PDA) plates, +/−amendments, were inoculated with selected pathogens as listed below in Table 18. There were several replicate plates used per treatment group (per pathogen tested). After incubation of plates at room temperature, fungal growth was measured.

TABLE 18

| Treatment | % Inhibition by C8 (C9) +/− Organic Acid | | | | | | | | | |
|---|---|---|---|---|---|---|---|---|---|---|
| | Late Blight | | *Alternaria* | | *Botrytis* | | *Pyth U.* | | White Mold | |
| Solution* | C8 | C9 | C8 | C9 | C8 | C9 | C8 | C9 | C8 | C9 |
| C8 or C9 | 85 | 61 | 48 | 41 | 57 | 39 | 57 | 48 | 96 | 93 |
| +glycolic acid 100% | 98 | 96 | 62 | 56 | 78 | 78 | 100 | 74 | 96 | 97 |
| +glycolic acid, 70% (tech) | 99 | 91 | 62 | 59 | 86 | 76 | 100 | 74 | 96 | 97 |
| +gluconic acid | 91 | 90 | 45 | 53 | 90 | 43 | 94 | 61 | 87 | 83 |

*The treatment solution was added to PDA
C8, caprylic acid, and
C9, pelargonic acid, at 0.025% in PDA (potato dextrose agar) plates
Organic acids at 0.013% in PDA (acids at same dry wt. basis)
Both C8 and C9: 85% C8 or C9/15% 6915 (concentrated emulsions used in PDA)

The data above indicate that overall, caprylic acid (C8) (+/−organic acids) exhibited greater fungicidal activity than pelargonic acid (C9) (+/−organic acids).

As can be seen from the above, the present invention provides novel compositions useful for treating plants, and their fruits, vegetables, seeds and/or nuts to prevent or inhibit fungus growth and formation. The composition can be used either prophylatically to inhibit and prevent fungus growth and/or to treat existing fungus. It has been determined that the combination of a fatty acid and an organic acid different from the fatty acid provides unexpectedly high fungicidal activity. Further, it has also been determined that fungicidally effective agricultural formulations can be prepared containing as little as 0.01% v/v of the fatty acid. The formulations are effective against a wide spectrum of fungal species. Further the formulations exhibit little or no phytotoxicity toward crop producing plants when applied at fungicidally effective amounts.

The present invention contemplates modifications to the fungicide formulations as would occur to those skilled in the art without departing from the spirit of the present invention including combining the fungicide formulations with other agriculturally acceptable components either active or inactive. In addition, the fungicide formulations can be applied by various application methods, and at differing rates and on different plants as would occur to those skilled in the art.

What is claimed is:

1. A fungicide composition consisting essentially of: a fatty acid, or a salt thereof, having between 5 and 22 carbon atoms included in a fungicidally effective amount; an organic carboxylic acid, or a salt thereof, different from the fatty acid, said organic carboxylic acid selected from the group consisting of: mevalonic acid, glycolic acid, ketoglutaric acid, glutaric acid, glyceric acid, malonic acid, benzoic acid, trichloroacetic acid, pyruvic acid, cinnamic acid, formic acid, fumaric acid, isocitric acid, oxalacetic acid, acrylic acid, isobutyric acid, itaconic acid, humic acid, tetrahydrofurfuryl salicylic acid, diethylamine salicylic acid, fulvic acid, pentonic acid, gluconic acid, galactonic acid, hexonic acid, saccharic acid, ascorbic acid, bionic acid, alanine, glycine, isoleucine, leucine, methionine, phenylalanine, proline, tryptophan, valine, asparagine, cysteine, glutamine, serine, threonine, tyrosine, aspartic acid, glutamic acid, arginine, histidine and lysine and mixtures of these acids; and a carrier and at least one emulsifier, wherein the composition is capable of forming an emulsion upon mixing with water and exhibiting a synergistic fungicidal effect upon application.

2. The composition of claim 1 consisting essentially of the fatty acid in an amount between about 1% v/v and about 99% v/v, based upon the total volume of the composition.

3. The composition of claim 1 wherein the fatty acid is selected from the group consisting of: pentanoic acid, hexanoic acid, heptanoic acid, octanoic acid, pelargonic acid, decanoic acid, undecanoic acid, lauric acid, myristic acid, palmitic acid, stearic acid, oleic acid, linolenic acid, linoleic acid, erucic acid, palmitoleic acid, pentadecanoic acid, margaric acid, arachidic acid, arachidonic acid, behenic acid, mixtures thereof.

4. The composition of claim 1 wherein the alkyl group of the organic carboxylic acid is a straight chain, branched chain or cyclic alkyl group.

5. The composition of claim 1 wherein the fatty acid is selected from the group consisting of: caprylic acid and pelargonic acid.

6. The composition of claim 5 wherein the organic carboxylic acid is selected from the group consisting of: glycolic acid, tetrahydrofurfuryl salicylic acid, diethylamine salicylic acid, and mixtures of these acids.

7. The composition of claim 5 wherein the organic carboxylic acid is selected from the group consisting of: pentonic acid, gluconic acid, galactonic acid, hexonic acid, saccharic acid, ascorbic acid, bionic acid, and mixtures thereof.

8. The composition of claim 5 wherein the organic carboxylic acid is selected from the group consisting of: fumaric acid, isocitric acid, ketoglutaric acid, oxalacetic acid and mixtures thereof.

9. The composition of claim 5 wherein the organic carboxylic acid is selected from the group consisting of: alanine, glycine, isoleucine, leucine, methionine, phenylalanine, proline, tryptophan, valine, asparagine, cysteine, glutamine, serine, threonine, tyrosine, aspartic acid, glutamic acid, arginine, histidine and lysine or mixtures thereof.

10. The composition of claim 1 consisting essentially of an organic carboxylic acid in an amount between about 0.01% v/v and about 80% v/v based upon the total volume of the composition.

11. The composition of claim 1 consisting essentially of the fatty acid and organic carboxylic acid in a weight ratio of between 1:1000 and about 1000:1.

12. The composition of claim 1 consisting essentially of the fatty acid and organic carboxylic acid in a weight ratio of between 1:5 and about 5:1.

13. The composition of claim 1 wherein the organic carboxylic acid is a dicarboxylic acid.

14. The composition of claim 1 wherein the organic carboxylic acid is an aromatic carboxylic acid.

15. The composition of claim 1 wherein the organic carboxylic acid is selected from the group consisting of mevalonic acid, glycolic acid, glyceric acid, benzoic acid, trichloroacetic acid, pyruvic acid, cinnamic acid, formic acid, acrylic acid, isobutyric acid, humic acid, tetrahydrofurfuryl salicylic acid, diethylamine salicylic acid, fulvic acid, pentonic acid, gluconic acid, galactonic acid, hexonic acid, ascorbic acid, bionic acid, alanine, glycine, isoleucine, leucine, methionine, phenylalanine, proline, tryptophan, valine, asparagine, cysteine, glutamine, serine, threonine, tyrosine, arginine, histidine and lysine.

16. The composition of claim 1 wherein the organic carboxylic acid includes an hydroxyl substituent.

17. The composition of claim 1, further consisting essentially of one or more of an adjuvant and/or a diluent.

18. The composition of claim 1 wherein the carrier is selected from the group consisting of: water, kerosene, xylene, mineral oil, vegetable or seed oil, alcohol and a mixture thereof.

19. The composition of claim 1 provided as a concentrate suitable for dilution, said composition consisting essentially of one or more emulsifier selected to suspend the fatty acid, or the organic carboxylic acid, or both in water upon dilution to provide a ready-to-use formulation.

20. The composition of claim 1 provided as a ready-to-use formulation suitable for application to harvested fruit, vegetables, berries, seeds, leaves, flowers and nuts.

21. The composition of claim 20 consisting essentially of the fatty acid in an amount between about 0.001% v/v and about 3.0% v/v, based upon the total volume of the composition.

22. The composition of claim 21 consisting essentially of the fatty acid in an amount between about 0.01% v/v and about 1.0% v/v, based upon the total volume of the composition.

23. The composition of claim 20 consisting essentially of the organic carboxylic acid in an amount between about 0.001% v/v and about 4.0% v/v, based upon the total volume of the composition.

24. The composition of claim 20 consisting essentially of the organic carboxylic acid in an amount between about 0.1% v/v and about 1.0% v/v, based upon the total volume of the composition.

25. The composition of claim 20 suitable for application to fruits, vegetables, berries, seeds or nuts after harvesting.

26. A method of controlling fungus, said method comprising contacting one or more of: fruit, vegetables, berries, seeds, and nuts with an effective amount of a ready-to-use composition prepared by diluting the composition of claim 1 with water.

27. A method of treating a crop product to inhibit fungal infection, said method comprising applying to the crop product a fungicidal composition of claim 1.

28. The method of claim 27 wherein the crop product is selected from the group consisting of: fruit, vegetable, berry, seed, nut, and flower.

29. The method of claim 27 comprising applying the fungicidal composition to the crop product after harvesting.

30. The method of claim 27 comprising applying the fungicidal composition to one or more of: strawberries, raspberries, blueberries, melons, stone fruit, nut crops, potatoes, vegetables, turf grasses, seed crops, corn, rice, wheat, soybeans, dry beans, peanuts, cotton, sorghum, and curcurbits.

31. The method of claim 27 comprising identifying crop product susceptible to fungal infection and applying the fungicidal composition to the crop product in one or more treatments.

32. The method of claim 27 wherein the crop product is dipped in the fungicidal composition.

* * * * *